US010779743B2

(12) United States Patent
van Dam et al.

(10) Patent No.: US 10,779,743 B2
(45) Date of Patent: Sep. 22, 2020

(54) ESTIMATING DISTRIBUTION, FLUCTUATION AND/OR MOVEMENT OF ELECTRICAL ACTIVITY THROUGH A HEART TISSUE

(71) Applicant: Peacs B.V., Arnhem (NL)

(72) Inventors: Peter Michael van Dam, Arnhem (NL); Eelco Mattias van Dam, Arnhem (NL)

(73) Assignee: PEACS B.V., Arnhem (NL)

( * ) Notice: Subject to any disclaimer, the term of this patent is extended or adjusted under 35 U.S.C. 154(b) by 167 days.

(21) Appl. No.: 14/270,899

(22) Filed: May 6, 2014

(65) Prior Publication Data

US 2015/0320331 A1   Nov. 12, 2015

(51) Int. Cl.
*A61B 5/0452* (2006.01)
*A61B 5/055* (2006.01)
*A61B 6/03* (2006.01)
*A61B 5/0408* (2006.01)
*A61B 5/0402* (2006.01)
*A61B 5/04* (2006.01)
*A61B 5/00* (2006.01)
*A61B 5/06* (2006.01)

(52) U.S. Cl.
CPC ......... *A61B 5/0452* (2013.01); *A61B 5/0402* (2013.01); *A61B 5/04012* (2013.01); *A61B 5/04085* (2013.01); *A61B 5/055* (2013.01); *A61B 6/03* (2013.01); *A61B 5/065* (2013.01); *A61B 5/7425* (2013.01)

(58) Field of Classification Search
CPC ......... A61B 5/0452; A61B 6/03; A61B 5/055; A61B 5/0402
See application file for complete search history.

(56) References Cited

U.S. PATENT DOCUMENTS

| | | | |
|---|---|---|---|
| 6,575,969 B1 * | 6/2003 | Rittman, III | A61B 18/1482 128/898 |
| 7,382,907 B2 * | 6/2008 | Luo | G06T 7/0012 382/128 |
| 8,155,739 B2 * | 4/2012 | Keel | A61B 5/11 607/9 |
| 2002/0105516 A1 | 8/2002 | Tracy | |

(Continued)

OTHER PUBLICATIONS

Geselowitz, David B., "Description of Cardiac Sources in Anisotropic Cardiac Muscle: Application of Bidomain Model," Journal of Electrocardiology, vol. 25, pp. 65-67.

(Continued)

*Primary Examiner* — Hien N Nguyen
(74) *Attorney, Agent, or Firm* — Foley and Lardner LLP

(57) ABSTRACT

A computer implemented method for processing measurement data from electrocardiogram, ECG, electrodes on a subject. The method includes obtaining a 3D anatomical model of the torso of the subject, and obtaining a 3D image of the torso of the subject. The three dimensional image is aligned with the three-dimensional model. A position of each electrode in the three-dimensional model is determined from the three dimensional image. The positions of the electrodes in the three dimensional model are used for estimating the distribution, fluctuation and/or movement of electrical activity through heart tissue.

13 Claims, 8 Drawing Sheets

(56) References Cited

U.S. PATENT DOCUMENTS

| | | | |
|---|---|---|---|
| 2002/0128565 A1* | 9/2002 | Rudy | A61B 5/0422 600/509 |
| 2005/0096515 A1 | 5/2005 | Geng | |
| 2006/0079759 A1 | 4/2006 | Vaillant et al. | |
| 2006/0224071 A1* | 10/2006 | Stewart | A61B 5/0006 600/509 |
| 2009/0088655 A1 | 4/2009 | Vajdic et al. | |
| 2010/0070249 A1 | 3/2010 | Ionasec et al. | |
| 2011/0060576 A1 | 3/2011 | Sharma et al. | |
| 2012/0157822 A1 | 6/2012 | Van Dam et al. | |
| 2012/0235993 A1 | 9/2012 | Kim | |
| 2012/0283587 A1* | 11/2012 | Gosh | A61B 5/0402 600/510 |
| 2013/0060315 A1* | 3/2013 | Elghazzawi | A61B 5/0077 607/142 |
| 2013/0177223 A1 | 7/2013 | Lee et al. | |
| 2013/0197881 A1 | 8/2013 | Mansi et al. | |
| 2013/0304407 A1* | 11/2013 | George | G01R 25/00 702/72 |
| 2014/0121636 A1* | 5/2014 | Boyden | A61M 5/427 604/506 |
| 2014/0207005 A1 | 7/2014 | Bukkapatnam et al. | |
| 2015/0356742 A1 | 12/2015 | Barbarito et al. | |
| 2017/0071675 A1 | 3/2017 | Dawoud et al. | |

OTHER PUBLICATIONS

Geselowitz, David B., "On the Theory of the Electrocardiogram," Proceedings of the IEEE, vol. 77, No. 6, Jun. 1989, pp. 857-876.

Huiskamp et al., "Heart Position and Orientation in Forward and Inverse Electrocardiography," Med Biol Eng Comput 30, 1992, 8 pages.

Mahmoud et al., "Interhospital Transfer Due to Failed Prehospital Diagnosis for Primary Percutaneous Coronary Intervention: an Observational Study on Incidence, Predictors, and Clinical Impact," European Heart Journal: Acute Cardiovascular Care 2(2), 2013, pp. 166-175.

Van Dam et al., "A New 3D Patient Specific Morphing Tool Enabling Clinical Application of Non-Invasive Cardiac Activation Imaging," 1 page.

Van Dam et al., "Application of the Fastest Route Algorithm in the Interactive Simulation of the Effect of Local Ischemia on the ECG", Med Biol Eng Comput 47, Published online Sep. 3, 2008, 10 pages.

Van Dam et al., "Non-Invasive Imaging of Cardiac Activation and Recovery," Annals of Biomedical Engineering, vol. 37, No. 9, Sep. 2009, pp. 1739-1756.

Van Dam et al., "Quantitative Localization of Premature Ventricular Contractions using Myocardial Activation ECGI from the Standard 12-Lead Electrocardiogram," Journal of Electrocardiology, 2013, pp. 574-579.

Van Oosterom, A., "Genesis of the T Wave as Based on an Equivalent Surface Source Model," Journal of Electrocardiology, vol. 34S, 2001, pp. 217-227.

Van Oosterom, A., "The Equivalent Double Layer: Source Models for Repolarization," Springer-Verlag London Limited, 2011, pp. 227-246.

Wilson et al., "The Distribution of the Action Currents Produced by Heart Muscle and Other Excitable Tissues Immersed in Extensive Conducting Media," The Journal of General Physiology, Published Jan. 20, 1933, pp. 423-456.

Han et al., Enhanced Computer Vision, Microsoft Kinect Sensor: A Review, IEEE Transactions on Systems, Man and Cybernetics, Part B, IEEE Transactions on Cybernetics, vol. 43, No. 5, Oct. 2013, pp. 1318-1334.

Huiskamp et al., The depolarization sequence of the human heart surface computed from measured body surface potentials. IEEE Transactions on Biomedical Engineering. Dec. 1988;35(12): pp. 1047-1058. PubMed PMID: 3220498.

Meijs et al., . On the Numerical Accuracy of the Boundary Element Method. IEEE Transactions on Biomedical Engineering, Oct. 1989;BME-36, vol. 10, pp. 1038-1049.

Oostendorp et al., Interpolation on a triangulated 3D surface. Journal of Computational Physics. 1989;80(2): pp. 331-343.

Swihart et al., Numerical Methods for solving the forward problem in electrocardiography, The Theoretical Basis of Electrocardiology, Nelson CV, Geselowitz DB, editors. Oxford: Clarendon Press; 1976, pp. 257-293.

Van Oosterom, et al., The Influence of Heart Position and Orientation on Body Surface Potentials. Journal of Electrocardiography vol. 24, No. 3, Jul. 1991, 3 pages.

Van Oosterom, The Equivalent Surface Source Model in its Application to the T Wave, Electrocardiology '01; 2002: Univ Press São Paolo, 6 pages.

"12 Lead ECG Placement example," YouTube video, published Feb. 18, 2015 [retrieved on 2018-20-23]. Retrieved from the Internet<URL:https://www.youtube.com/watch?v=0gAOy712-Gs>.

Lieberman, "Interpreting 12-Lead ECGs: A Piece by Piece Analysis" The Nurse Practitioner, vol. 33 (2008) pp. 28-35.

Poerner et al., "Physiological Range of Mechanical Synchronicity of the Human Heart: Comparison Between Different Echocardiographic Assessment Modalities," Ultrasound in Med. And Biol., vol. 31, 2005, pp. 1163-1172.

Prassl et al., "Automatically Generated, Anatomically Accurate Meshes for Cardiac Electrophysiology Problems," (IEEE Transactions on Biomedical Engineering, vol. 56, 2009, pp. 1318-1330.

Rantner et al., "Placement of implantable cardioverter-defibrillators in paediatric and congenital heart defect patients: a pipeline for model generation and simulation prediction of optimal configurations," J. Physical, vol. 591, 2013, pp. 4321-4334.

Zalenski et al., "Value of Posterior and Right Ventricular Leads in Comparison to the Standard 12-Lead Electrocardiogram in Evaluation of St-Segment Elevation in Suspecte" The American Journal of Cardiology, vol. 79, Issue 12, Jun. 15, 1997, pp. 1579-1585.

Van Dam et al., "New Computer Program for Detecting 12 Lead ECG Misplacement Using a 3D Kinect Camera," Computing in Cardiology, 40, pp. 1175-1178 (2013).

Zhang et al., "3-Dimensional Activation Sequence Reconstruction from Body Surface Potential Maps by Means of a Heart-Model-Based Imaging Approach," Computers in Cardiology, 31, pp. 1-4 (2004).

* cited by examiner

ESTIMATING DISTRIBUTION, FLUCTUATION AND/OR MOVEMENT OF ELECTRICAL ACTIVITY THROUGH A HEART TISSUE

FIELD OF THE INVENTION

The invention relates to electrocardiogram (ECG) technology. More in particular the invention relates to generating a model of a heart using ECG measurements. More in particular the invention relates to estimating the distribution, fluctuation and/or movement of electrical activity through heart tissue. More in particular, the invention relates to locating heart dysfunction such as locating an origin of premature ventricular contraction (PVC) tachycardia (VT), atrial tachycardia (AT), Wolff-Parkinson-White syndrome (WPW) and conduction orders in a heart on the basis of ECG measurements.

BACKGROUND

The inventors have to date made progress in so called inverse computations where e.g. an activation sequence and/or other parameters of the heart are estimated from surface electrocardiograms. Inverse imaging of electrical activity of a heart muscle is for instance described in published patent application US-2012-0157822-A1.

The inventors devised a computer program, herein referred to as Cardiac Isochrone Positioning System (CIPS), which using only the standard 12-lead ECG quantitatively localizes the origin of PVCs in patients.

SUMMARY

CIPS can use any electrode position on the chest wall: consequently there are no misplaced electrodes. However, the exact location of the electrodes is critical to the outcome of CIPS. Therefore the inventors developed three-dimensional (3D) Camera software integrated into CIPS that localizes the ECG electrodes.

The accurate electrode positions are required by the cardiac isochrones positioning system. Therefore a 3D camera based system was developed to localize the electrodes.

The 3D camera is used to take 3D images of the torso of subjects with ECG electrodes attached. The software transforms the 3D quantitative image into a subject specific electrode torso model. These torso models were scaled to obtain an objective standard for electrode misplacement.

The 3D camera computer software automatically and rapidly detects misplacement of e.g. 12-lead ECGs electrodes.

The invention relates to a computer implemented method for processing measurement data from electrocardiogram, ECG, electrodes on a subject. The method includes obtaining a three-dimensional, 3D, anatomical model of the torso of the subject. Preferably, the anatomical model includes both an outer surface and positional information on internal structures such as the heart and lungs. The three-dimensional anatomical model of the torso of the subject can e.g. be derived from a medical imaging modality, such as MRI, CT, PET-CT, ultrasound, or the like.

The method also includes obtaining a three-dimensional image, such as a three-dimensional photograph, of the torso of the subject including position information of the electrodes. The three-dimensional image contains a three-dimensional representation of an outer surface of the torso of the subject. The three-dimensional image also includes position information on the electrodes positioned on the outer surface of the torso. The three-dimensional image may be obtained using a 3D camera. The three-dimensional image may e.g. be a three-dimensional photograph or video recording. The position information of the electrodes may be formed or derived from the electrodes being visible in the three-dimensional image. The three dimensional image is aligned with the three-dimensional model. The aligning can include minimizing the distances between the three-dimensional image and the three-dimensional model.

A position of each electrode in the three-dimensional model is determined from the position of each electrode in the overlain three dimensional image. Using the positions of the electrodes in the three dimensional model the distribution, fluctuation and/or movement of electrical activity through heart tissue are estimated.

According to an aspect of the invention, a position of each electrode in the three-dimensional model is determined from the aligned three dimensional image. The positions of the electrodes in the three dimensional model are used for estimating the distribution, fluctuation and/or movement of electrical activity through heart tissue.

A fastest route algorithm, in particular together with a equivalent double layer model, allows for so-called inverse functional imaging of electrical activity (activation, recovery) of a heart muscle, in particular of a complete image of a heart, as well as particular areas of interest both on the outside (epicardium) and inside (endocardium) of the heart or both. As an algorithm that may lead to comparable results as the fastest route algorithm, the fast marching algorithm, the shortest path algorithm, the ion kinetic model or the cellular automaton model may be used. This is for instance described in US2012/01257822, incorporated herein by reference.

An ECG is defined herein as any method that (preferably non-invasively) correlates actual electrical activity of the heart muscle to measured or derived (electrical activity) of the heart. In case of a classical electrocardiogram the differences in potential between electrodes on the body surface are correlated to the electrical activity of the heart. Derived ECG's can also be obtained in other ways (e.g. by measurement made by a so-called ICD (Implantable Cardioverter Defibrillator)). In order to obtain such a functional image an estimation of the movement of the electrical activity has to be provided.

According to an aspect, the method further includes determining an identification of each electrode from the three-dimensional image. The identification can be one of a color, a shape, or a code. The method can further include detecting positions of each a plurality of electrodes, comparing the detected positions with predetermined positions and determining whether the electrodes are positioned approximately in the correct predetermined position. Thus, it is for instance possible to determine whether or not the electrodes are positioned in swapped positions. Electrodes that are supposed to be positioned in an order V1, V2, V3, V4, may, e.g. be actually positioned in an order V1, V4, V3, V2. Once swapped positions have been detected, the program may take these swapped positions into account. The program may internally swap the signals received from the swapped electrodes so that the processed signals correspond to the correct electrode positions. Therefore a need for repositioning swapped electrodes may be obviated.

According to an aspect, the method includes indicating whether the electrodes are positioned in a desired position. The electrodes may e.g. be positioned inaccurately. The program may be arranged for indicating a direction and/or distance for repositioning an electrode.

When the underlying anatomy of the patient is known (e.g. from a MRI/CT model) the system can also be used to guide lead placement, i.e. make sure the electrodes are over the area of interest. This can be patient specific. For certain patients, (e.g. Brugada) it is known that the standard 12 lead ECG electrode positions do not measure the known deviations in the ECG. Electrodes need to be put higher in such case. How high can now be related to the cardiac anatomy underneath the electrodes. This will also help CIPS to improve the diagnosis for these patients.

BRIEF DESCRIPTION OF THE DRAWINGS

Embodiments of the present invention will now be described in detail with reference to the accompanying drawings.

DETAILED DESCRIPTION

CIPS can be used to localize the PVC origin or any other atrial or ventricular arrhythmia by electrodes accurately placed in the standard 12 lead ECG positions.

In this example the electrodes were moved up and down in 10 mm increments. For each of these moved electrode positions, CIPS was used to localize the PVC origins. This change in PVC origin location as determined by CIPS was compared to the displacement of the ECG electrodes. To investigate the registration reproducibility of CIPS, 5 images were registered manually to the MRI derived torso model on which the electrode positions were projected from the 3D image.

In seven patients, the PVC origin was localized correctly by CIPS to the ablation sites with accurately positioned electrodes. However, recorded changes in PVC origins varied greatly from 0 to 110 produced by 10 mm increments up to a range of 9-110 mm when moving the electrodes 30 mm down. The registration error of integrating the 3D image with the MRI derived torso model was less than 2.5 mm per electrode.

Using CIPS, even with a 10 mm change of the electrodes the error for localization of PVC are highly variable and large. The CIPS software that integrates and registers the 3D camera image of the electrodes to the MRI derived torso model is reproducible.

The 3D camera is useful for quantitative localization of electrode positions for CIPS to accurately localize the origins of the PVCs, ventricular tachycardia (VT), atrial tachycardia (AT), Wolff-Parkinson-White syndrome (WPW), conduction orders and Delta waves using the 12 lead ECG in the electrophysiology (EP) Lab and in the general clinical setting. This example highlights the advantage of relating the accurate position of the electrodes to the cardiac anatomy as imaged with the 3D camera instead of using the standard position of the rib interspaces.

Figure 1:
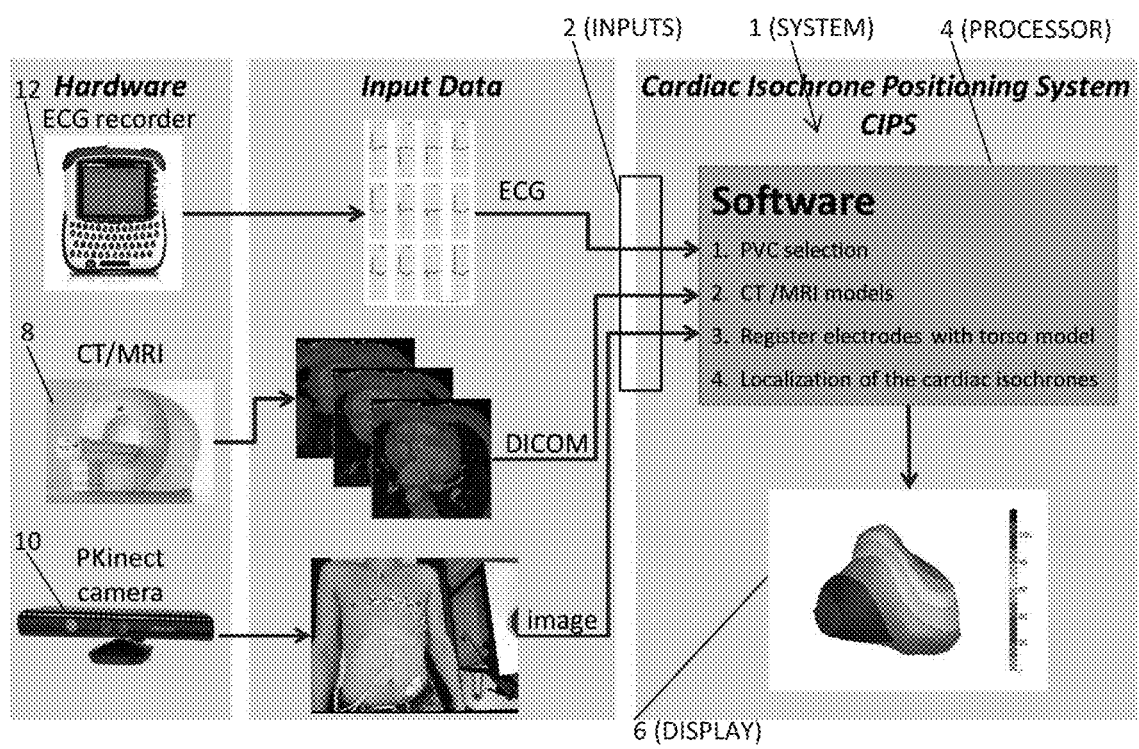
FIG. 1. Overview of the 4 modules of CIPS: PVC selection (equivalent to Selection of a single atrial or ventricular heart beat from the ECG), CT/MRI derived models, the in this application described new method to register the electrodes to the torso model derived from MRI/CT.

FIG. 1 shows a schematic overview of a system 1 according to the invention. The system includes a model input unit 2 for obtaining a three-dimensional, 3D, anatomical model of the torso of the subject. In FIG. 1 the 3D model data is obtained from a CT/MRI system 8. The system further includes an image input unit 2 for obtaining a three-dimensional image of the torso of the subject. In FIG. 1 the 3D image data is obtained from a 3D camera 10, here a Kinect camera. The system further includes an ECG input unit 2 for obtaining ECG data.

The system in FIG. 1 further includes a processor 4. The processor 4 is arranged for aligning the three dimensional image with the three-dimensional model, determining a position of each electrode in the three-dimensional model from the three dimensional image; and using the positions of the electrodes in the three dimensional model for estimating the distribution, fluctuation and/or movement of electrical activity through heart tissue.

The process performed by the processor, such as by a computer program running on the processor, is described herein below.

Selection of a Single Atrial or Ventricular Heart Beat from the ECG

Figure 2:
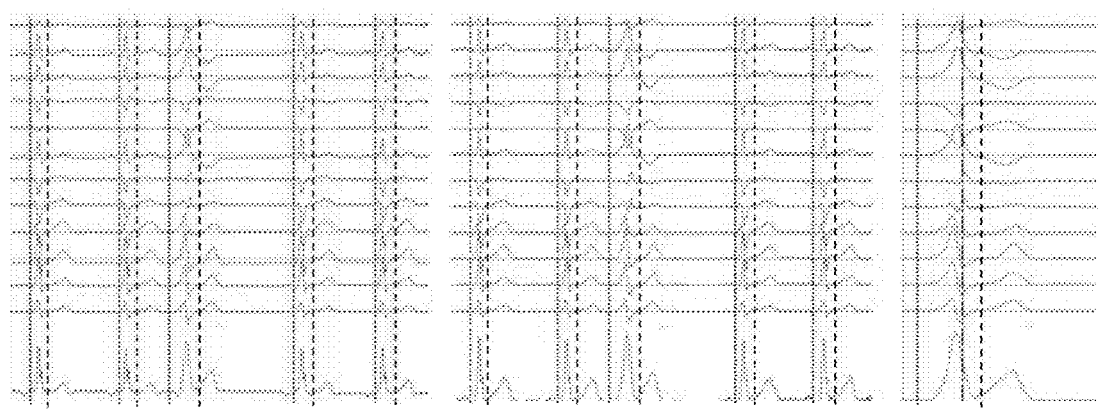
FIG. 2. Left detection of QRS's (dotted and dashed lines, middle base line corrected, and selected beat (right).

CIPS analyses single atrial or ventricular complexes. This requires a QRS detection algorithm and a baseline correction procedure. From these signals automatically or manually the clinical interesting beats can be selected for analysis (see FIG. 2). This selection is done using a first module. The first module is herein also referred to as selection module.

CT/MRI Derived Models

A second module describes the model creation and the way these models are used to compute an ECG on any location on or inside the thorax:

1) Cardiac current source model linked to cardiac electrophysiology (Equivalent double layer source model)

2) Volume conductor:
   a. proximity effect, spatial orientation of the 9 ECG electrodes
   b. inhomogeneous volume conductor
   c. Patient's specific geometry from Computed Tomography (CT) or Magnetic Resonance Imaging (MRI) (FIG. 1), The first component, the cardiac current source model, is the equivalent double layer (EDL). The EDL represents the currents generated by the cardiac tissue during activation and recovery, which is equivalent to the currents generated by all coupled myocardial cells as recorded at endo- and epicardial surfaces [1], [2]. Consequently, the EDL is referred to the localization at the endo- and epicardial surface of the myocardium. For any position (node) on the triangulated ventricular surface, the time course of the local source strength is taken to be proportional to the transmembrane potential (TMP) of the nearby myocytes [3], [4]. The second component accounts for the volume conductor effects, being: a) proximity and spatial orientation of the 9 ECG electrodes and b) the differences in conduction properties of the various tissues. The proximity effect and spatial orientation is determined by the solid angle of the active cardiac tissue as observed from the ECG electrodes [5]. The solid angle accounts for the fact that ECG waveforms of electrodes close to the heart are dominated by the cardiac tissue underneath depending on the direction of the wave front. Previous studies indicated that an appropriate volume conductor model requires the incorporation of the heart, blood cavities, lungs and thorax [6], [7]. In this example, the conductivity values σ assigned to the individual compartments were: thorax and ventricular muscle: 0.2 S/m, lungs: 0.04 S/m and blood cavities: 0.6 S/m. The mathematical method used to solve this volume conductor problem in a numerical way is referred to as the Boundary Element Method (BEM) [8], [9]. With the BEM a transfer matrix A can be computed taking into account the full complexity of the discretized volume conductor model. For the potentials at thorax node l of the 12-lead electrodes is defined by $$ECG(t;l) = \Sigma_n A(l,n) S(t; \delta_n, \rho_n),  \quad \text{EQ1}$$

in which $S(t; \delta_n, \rho_n)$ is the local time dependent EDL source strength, and $A(l,n)$ the BEM derived transfer function relating the contribution of S at node n to the potentials ECG at thorax node l, or in a matrix notation:

$$ECG = AS \quad \text{EQ2}$$

Estimation of Cardiac Activation and Recovery

A fourth module estimates the cardiac activation through a rough- and fine tuning algorithm described in described [10] and in published patent application US-2012-0157822-A1, incorporated herein by reference. Briefly:
   a. The fastest route based initial estimate of cardiac activation provides the rough initial estimate.
   b. Optimization procedure is used for the fine-tuning The fourth module relates to patient-specific geometric models of the heart, lungs and thorax derived from, e.g., Multi Slice Computer Tomography (MSCT) (see FIG. 1).

Previous studies have shown the importance of patient-specific models [11], [12]. These geometric models were created with morphing software [13]. With such software the boundaries of all relevant tissues were identified manually. For the ventricles these boundaries are the left- and right endocardium, epicardium, aorta and pulmonary artery. To capture the spatial orientation from the 12-lead electrodes, the epicardium and endocardium, lungs, and thorax are morphed to match the manual drawn contour points. This yields a patient specific geometry.

Figure 3:
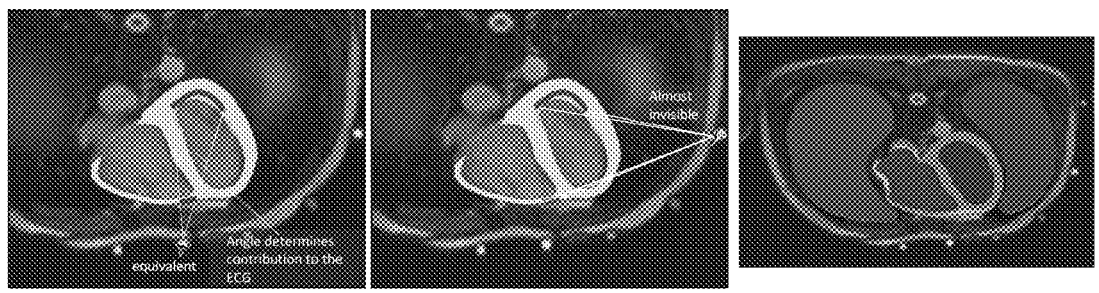
FIG. 3. The three volume conductor effects: a) proximity effect, b) spatial orientation, and c) volume conduction; bloods conducts better than myocardial tissue, lungs worse.

The fourth module uses output from the first and second modules as well as from a third module described below to, preferably automatically, position the activation isochrones on the endo- and epicardial ventricular surface. The rough tuning step is an adapted version of the fastest route to obtain an electrophysiological based initial estimate of the activation sequence as described previously [10], [14]. In short: One ore multiple foci are determined using the fastest route algorithm (see FIG. 3). For each node an activation sequence is computed using a QRS derived propagation velocity. The first estimate of the activation isochrones is the one with the highest correlation between the actual measured ECG and the model derived ECG. In the next iteration an extra focus is added. The activation sequence is computed by the "first come, first served" principle. This procedure is then repeated until there is no increase in correlation found. The final activation isochrones are obtained by a Levenberg-Marquardt based optimization procedure in which the rough tuned activation isochrones are tuned to obtain matching ECGs.

The $3^{rd}$ Module of CIPS: The 3D Camera to Locate and Register the Electrodes Automatically Localization of the ECG electrodes is important to reduce modeling errors, i.e. the transfer from the heart surface to the electrode positions on the chest surface. With a 3D camera, for instance a Kinect camera, the 3D reconstruction of an object is be created (see FIG. 4). This reconstructed shell of the thorax is be used to create a 3D overlay to the thorax derived from MRI/CT (second module).

As CIPS needs location information of each the electrodes on the chest surface for every ECG recording it wants to analyze, an algorithm for automatically determining the location of each electrode is used in this example.

Thereto, the system is further provided with a 3D camera. The 3D camera obtains a 3D image of the torso of a patient. The 3D image of the patient provides patient specific 3D data of the outer surface of the torso of the patient. The 3D image contains spatial information in three dimensions on the outer surface of the torso of the patient. According to the invention the patient specific 3D torso data is aligned to a 3D torso model of that patient derived from MRI in the EP laboratory. This allows for the accurate localization of PVCs by the Cardiac Isochrones Positioning System.

Further, the 3D camera provides location data of the electrodes visible in the field of view of the 3D camera. The location data includes position data in three dimensions for each electrode within the field of view of the 3D camera. Additionally, the 3D camera can be arranged to identify an identifier of each of the electrodes within the field of view of the 3D camera. The identifier can e.g. be a color, a shape, a number, a code or the like. Preferably each electrode has a unique identifier. The identifier of the electrode associated with a certain channels of the ECG is made known to the system. For instance the channels/electrodes are color-coded. Thus, the position of each electrode can be detected automatically. Currently different color codes are used for the 12 lead ECG system.

Thus, the invention provides for to the automatic alignment of a 3D image of the patient torso with the patient specific 3D model of the torso. The invention also provides for the automatic detection of electrode positions on the chest wall.

The 3D image of the torso is automatically aligned to the 3D torso model derived from MRI/CT using a minimization procedure in which the distance between the image points in the 3D image and model points in the torso model is reduced automatically. Once aligned, the head of the patient can be removed automatically to ensure the patient privacy. This might be a requirement as photos of the patient are taken. In this example, on the basis all 3D image data above the shoulders is thereto removed. As the position of the shoulders is known from the 3D torso model, this head removal can be automated in the system.

Next, electrode positions need to be located accurately on the 3D model of the torso. In this example colored electrodes are used. The electrode positions can then be automatically detected using the color as an identifying marker. Other identifying markers like text etc., can be used as well. In the absence of electrode identifiers, the program can determine the electrode positioned closest to a predefined (e.g. optimum) electrode location, define this electrode as coupled to that predefined location, and determine the actual location of that electrode on the basis of the 3D image.

Notice that for every ECG recording a 3D image is required, as electrodes can be place anywhere on the chest wall.

The ECG based Cardiac Isochrones Positioning System (CIPS) for example uses nine electrodes. The electrode positions on the torso are determined to estimating the distribution, fluctuation and/or movement of electrical activity through heart tissue, e.g. to localize accurately the origin of the PVC, VT, AT and delta waves [15]. However, in the EP lab the electrodes are frequently not placed in the predetermined positions. An example of such predetermined positions are the standard twelve lead ECG positions. Placing the electrodes in other positions than the predetermined positions can be due to other attached system's patches. The system includes a 3D camera and 3D camera software that automatically detects electrode misplacement. Optionally the program is further arranged to correct for such misplacements. The 3D quantitative image data is used to construct a subject specific torso geometry. To be able to compare electrode misplacement among subjects, in this example the torso models were scaled to a standard height, assuming the ribcage scales linearly with torso height. The triangulated torso geometry was additionally used to correct the ECG signals from the misplaced electrodes.

EXAMPLE

In this example software is used using the Microsoft Kinect software development kit (SDK) version 1.7. However, it will be appreciated that other 3D cameras and software kits can be used. This software retrieves the data from the Kinect camera [16] and processes the data to obtain the subject specific torso models.

Measurement Setup

To test the ability to detect electrode misplacement from 3D image derived torso models, five subjects were included in this example study. On each subject the 12 lead electrodes were positioned accurately by an experienced technician. Additionally the precordial electrodes were positioned one intercostal space higher and one intercostal space lower (see FIG. 8). Extremity electrode positions were unaltered during the ECG recording. For each configuration the ECG was recorded while the subject maintained a supine position.

Figure 8:
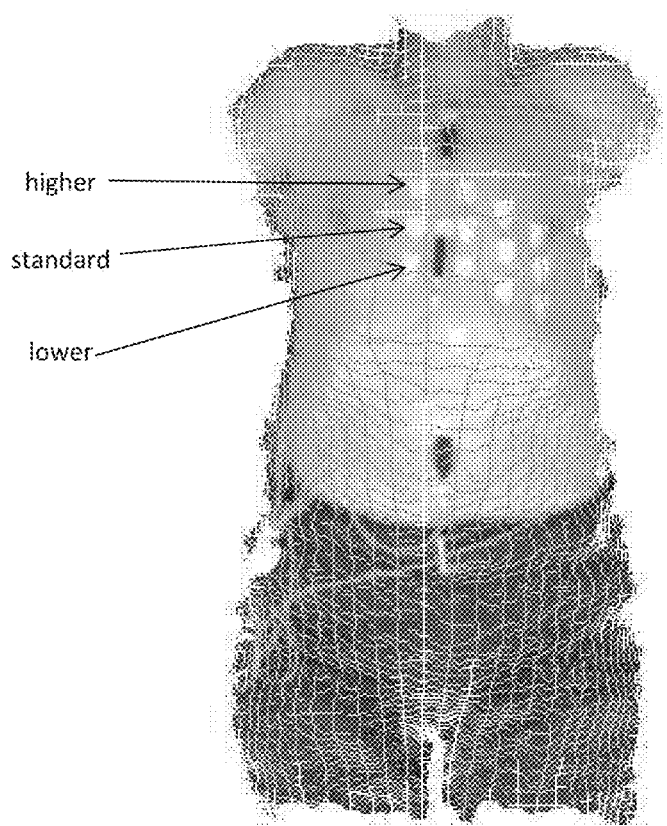
FIG. 8. 3D image as taken with the Kinect camera. Clearly visible are the electrodes of V1-V4 at the standard positions and one intercostal space below and above.

In FIG. 8 is the 3D image of a subject recorded in the Antero-posterior position with the attached electrodes. Therefore the accuracy of the V5 and V6 electrodes could not be determined.

Torso Model Construction to Detect Electrode Misplacement

In order to make a 3D computer model, in this example triangles are used to describe the surface of the human torso. To detect the misplacement of the electrodes a common reference point must be created. This requires the definition of a reference point. For the reference model the z-coordinate of the reference point was defined at a quarter of the height of the torso model (FIG. 10B). The height of the torso was taken as the distance between the shoulders and the crotch. The center of the horizontal plane at the middle of the torso resulted in the x-coordinate and y-coordinate of the reference point. All subsequent torso models were scaled to match the height of the common reference model. The distance in the z direction with respect to the reference point was used to detect the misplacement of leads.

Method for ECG Lead Correction

Three common electrode misplacements configurations were used to reconstruct the ECG signals at the standard positions:
1) V1,2 higher, V3 standard, and V4-6 lower
2) V1,2 and V6 standard, and V3-5 higher
3) V1-3 higher, and V4-6 standard The ECGs recorded at these misplaced electrode positions were used to reconstruct the ECGs at the standard positions with a surface laplacian based interpolation method [17].

The differences between reconstructed and recorded 12 lead ECG data were quantified using the relative difference (rd) measure: the root mean square value of all matrix elements involved relative to those of the recorded ECG data.

Results

As seen in table 1, the KINECT torso models derived chest circumferences had a close calibration to the measured chest circumferences. The distance between the standard electrodes and the electrodes placed one intercostal space above was 43±3.5 mm and 42±3.5 mm for the electrodes below.

TABLE 1

Calibration of the 3D camera measurement: The chest circumference directly measured was compared with the 3D camera measurements. The circumference was measured at the height of 4th intercostal space and from the reconstructed torso model at approximately the same height. Note their similarity.

| subject | age (years) | Chest circumference (cm) | | height (cm) |
|---|---|---|---|---|
| | | measured | 3D camera | |
| KP001 | 65 | 108 | 110 | 188 |
| KP002 | 54 | 107 | 110 | 186 |
| KP003 | 21 | 87 | 91 | 173 |
| KP004 | 41 | 84 | 91 | 177 |
| KP005 | 42 | 85 | 90 | 192 |

Figure 10A:
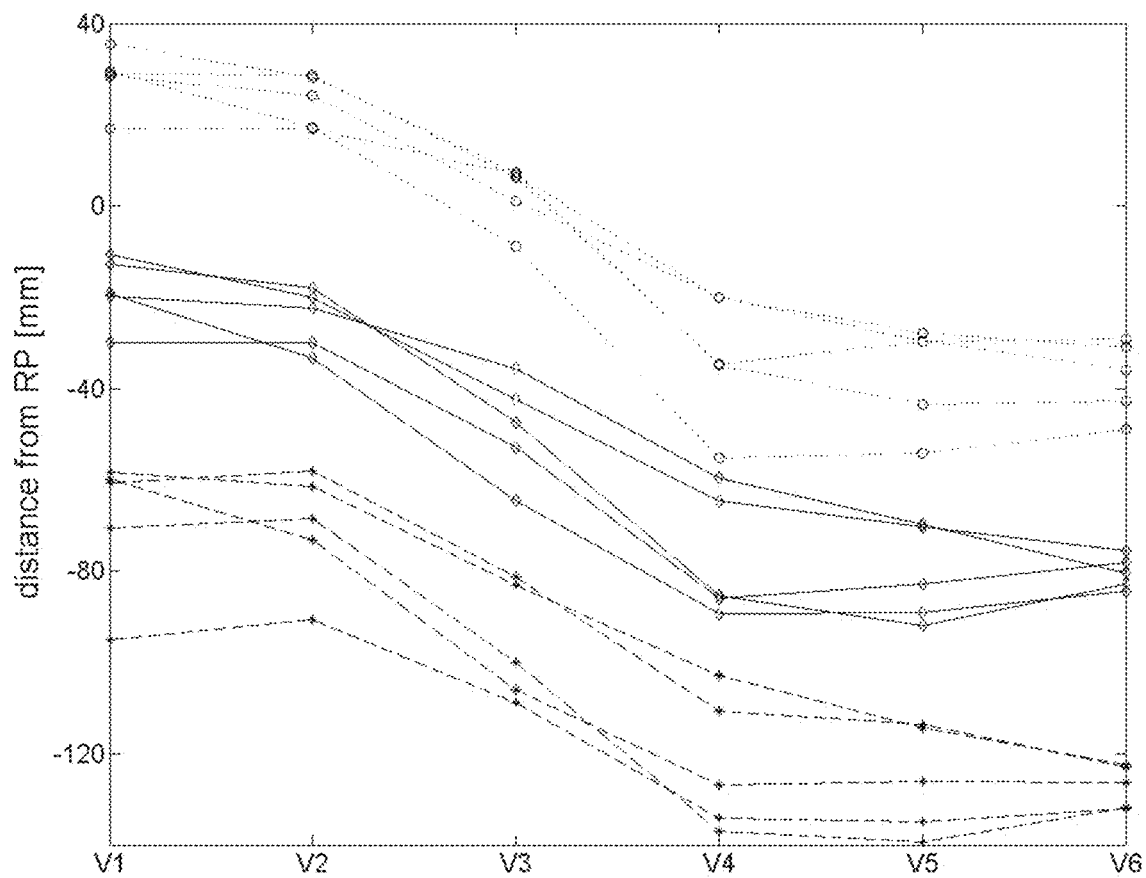
FIG. 10A. the scaled height of the electrodes of the precordial leads with respect to the reference point of all 5 subjects. In solid lines the electrodes at the standard positions, in dotted lines electrodes were shifted one intercostal space up and in dashed lines one intercostal space lower.
Figure 10B:
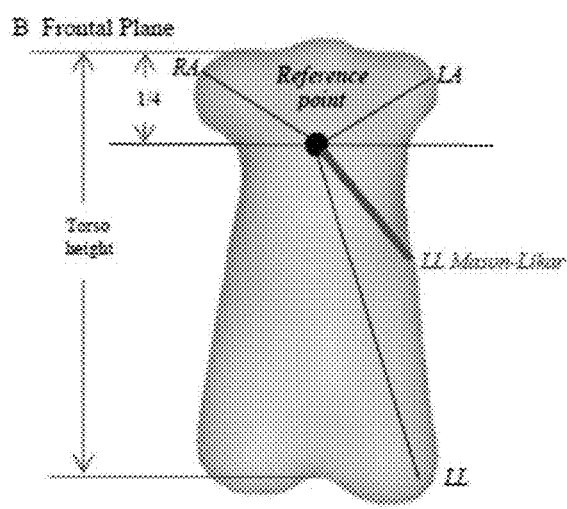
FIG. 10B. Extremity leads shown in the frontal plane. The thick line indicates the location of the LL electrode in the Mason-Likar position, which can easily be detected.

As shown in FIG. 10A, the electrodes placed one intercostal space above or below were calculated by the program to be significantly misplaced using the distance from leads V1-V6 to the reference point (P≤0.01).

Figure 4:
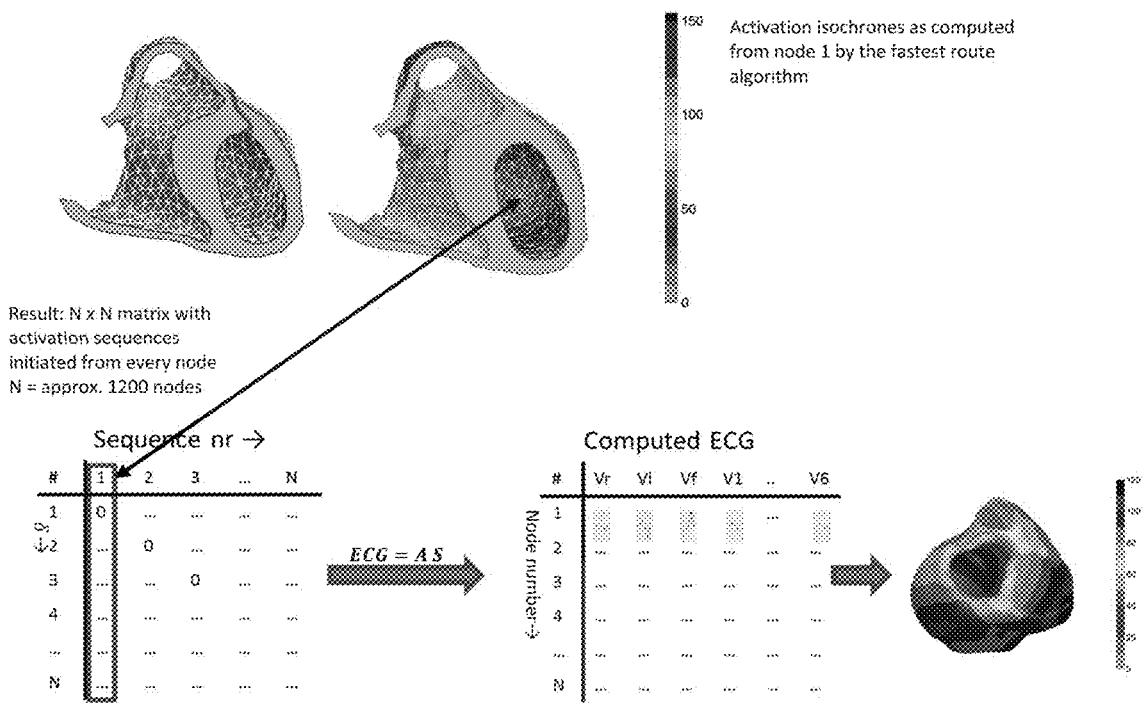
FIG. 4. Rough tuning of the first activation sequence: For each node and node on the heart an activation sequence is created (left matrix). From these activation sequences the ECG can be computed (Eq 2). The activation (node) resulting in the highest correlation between measured and simulated ECG is taken as the initial estimate.
Figure 5:
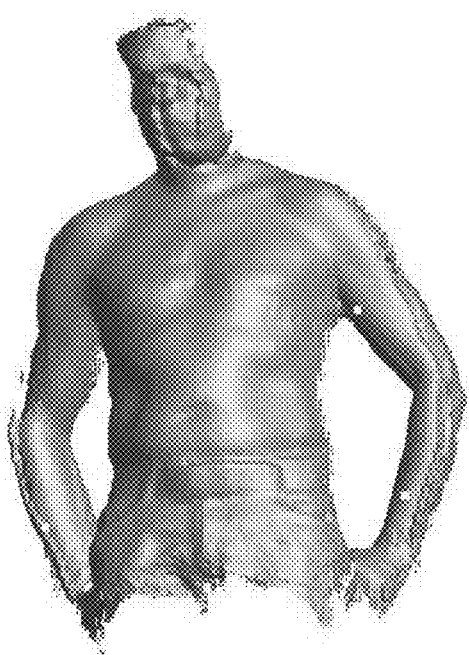
FIG. 5. Reconstruction of a torso with a 3D camera.
Figure 6:
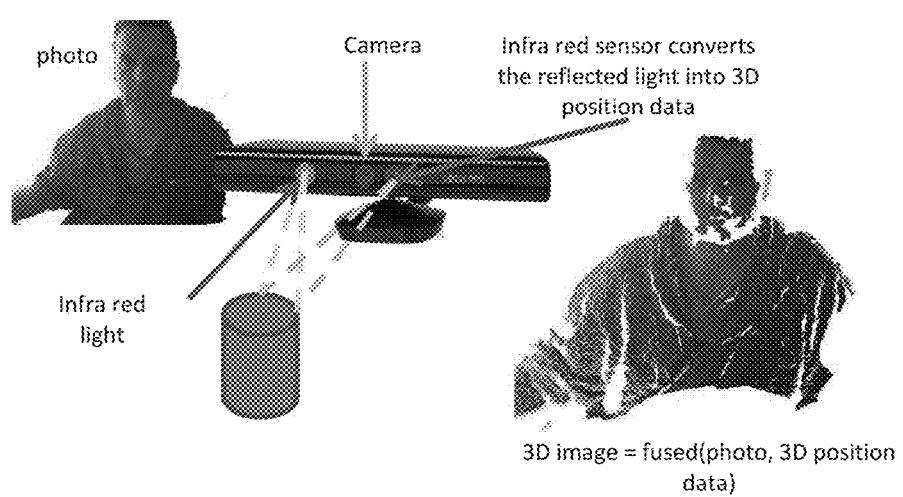
FIG. 6. How the 3D camera works.
Figure 7:
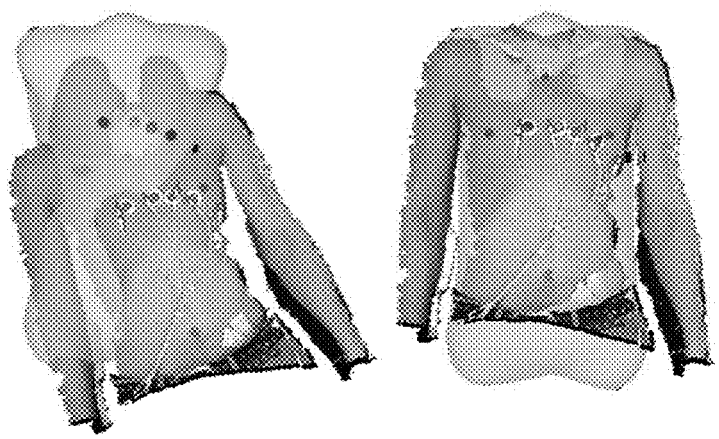
FIG. 7. Alignment of 3D image with torso model.
Figure 9:
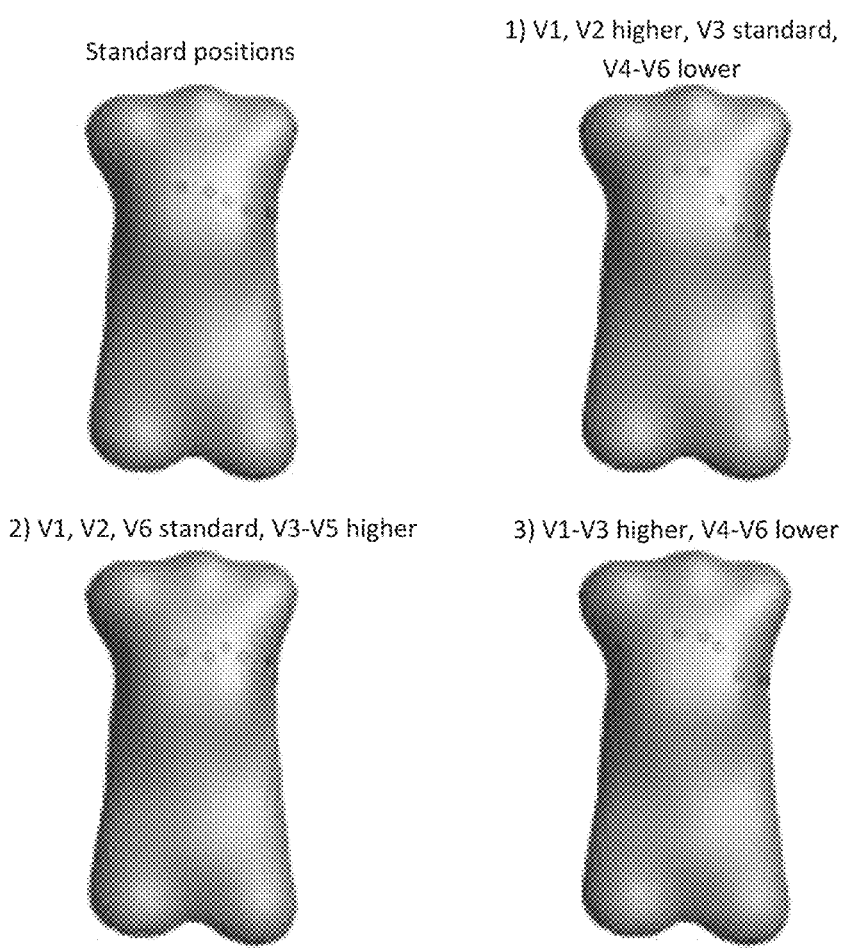
FIG. 9. Torso models with electrodes: The standard 12 lead ECG positions and the three misplaced electrode configurations 1), 2), and 3).

The standard 12 lead ECGs were reconstructed from the three different misplaced lead configurations (FIG. 9). In table 2 the relative differences (rd) are listed for all subjects and the 3 different lead configurations. In five cases the rd increases, in all other cases the rd did improve. Only in 4 cases the rd was below 0.2, a value that corresponds to a correlation coefficient of more than 98%. Especially for lead configuration 1 the interpolation failed to reconstruct the standard 12 lead ECG accurately. An example of the reconstruction of the ECG at the standard positions from the third misplaced lead configuration is shown in FIG. 4. As shown in FIG. 5 the misplaced leads V2 and V3 are corrected by interpolation but not in V1.

TABLE 2

Correction of misplaced electrode ECGs: Relative difference (rd) before and after correction of the ECG signals. See FIG. 2 for the used lead misplacement configurations. A rd of 0.2 corresponds to a correlation coefficient of more than 98%.

|       | 1      |       | 2      |       | 3      |       |
|-------|--------|-------|--------|-------|--------|-------|
|       | before | after | before | after | before | After |
| KP001 | 0.37   | 0.44  | 0.22   | 0.20  | 0.28   | 0.47  |
| KP002 | 0.24   | 0.27  | 0.34   | 0.34  | 0.21   | 0.26  |
| KP003 | 0.23   | 0.26  | 0.20   | 0.09  | 0.24   | 0.19  |
| KP004 | 0.23   | 0.27  | 0.20   | 0.13  | 0.24   | 0.22  |
| KP005 | 0.41   | 0.26  | 0.39   | 0.24  | 0.36   | 0.15  |

The 3D camera proves to be an appropriate tool to obtain the torso geometry including the electrode positions on the chest wall. Thus this tool enables the patient specific torso reconstruction in the EP laboratory, a requirement for the accurate localization of PVCs by the Cardiac Isochrones Positioning System [15].

It is possible to detect electrode misplacement by using the visual information recorded by a 3D camera. The precordial electrodes located approximately 4 cm from the standard positions could be significantly classified as misplaced (FIG. 10). When using a database containing rd data the sensitivity and specificity of distances and angles misplaced leads can be determined accurately, and corrected position information for the misplaced leads can be estimated accurately.

In this example, the major underlying assumption in the Torso Model is that the height of the ribcage, and consequently the standard precordial electrode positions scales linearly with the torso length. This assumption is adequate to detect the electrode misplacement. Furthermore, other landmarks of the torso, such as the angle of Louis or the xyphoid, might be mathematically derived from these models as well.

Correct electrode placement of the 12 lead ECG is critical for correct computerized ECG diagnoses systems. The likelihood of misplacement can be incorporated in computerized ECG analysis algorithms, thus increasing the sensitivity and specificity of the applied ECG diagnosis algorithms. As shown in FIG. 10B, the detection of the left leg (LL) electrode in the Mason-Likar position between the mid-left lower ribcage and the iliac crest.

This position can be converted by the program to the standard position on the left leg. This lead misplacement algorithm can also be applied in ambulances with equipment that transmit the acquired ECG's digitally to a hospital for on-line consulting and diagnosis.

In a significant percentage of the patients suffering from acute coronary syndrome the diagnosis based on the transmitted ECG's is incorrect [18]. This might result in the transportation of these patients to a hospital where a percutaneous coronary intervention (PCI) procedure cannot be performed. Using the 3D camera to detect electrode misplacement and the use of the program to correct the diagnosis could reduce the number of patients transported to the wrong facility.

Figure 11:
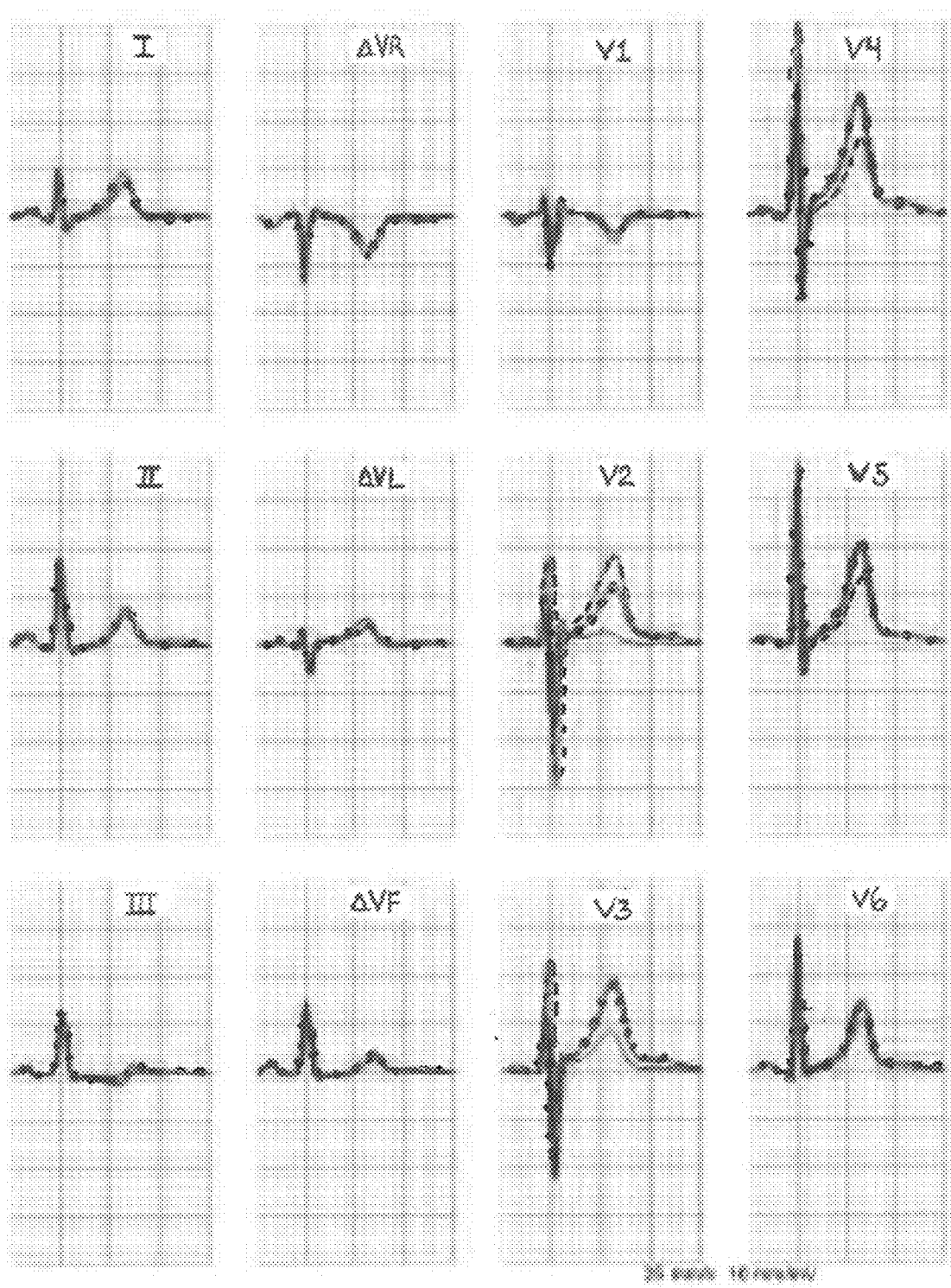
FIG. 11. Precordial electrodes one intercostal space higher and lower: The standard 12 lead ECG of case 4 (dotted line) one intercostal space higher (solid line) and one intercostal space lower (dashed line). Note: the major differences in V1-4 that need to be corrected.
Figure 12:
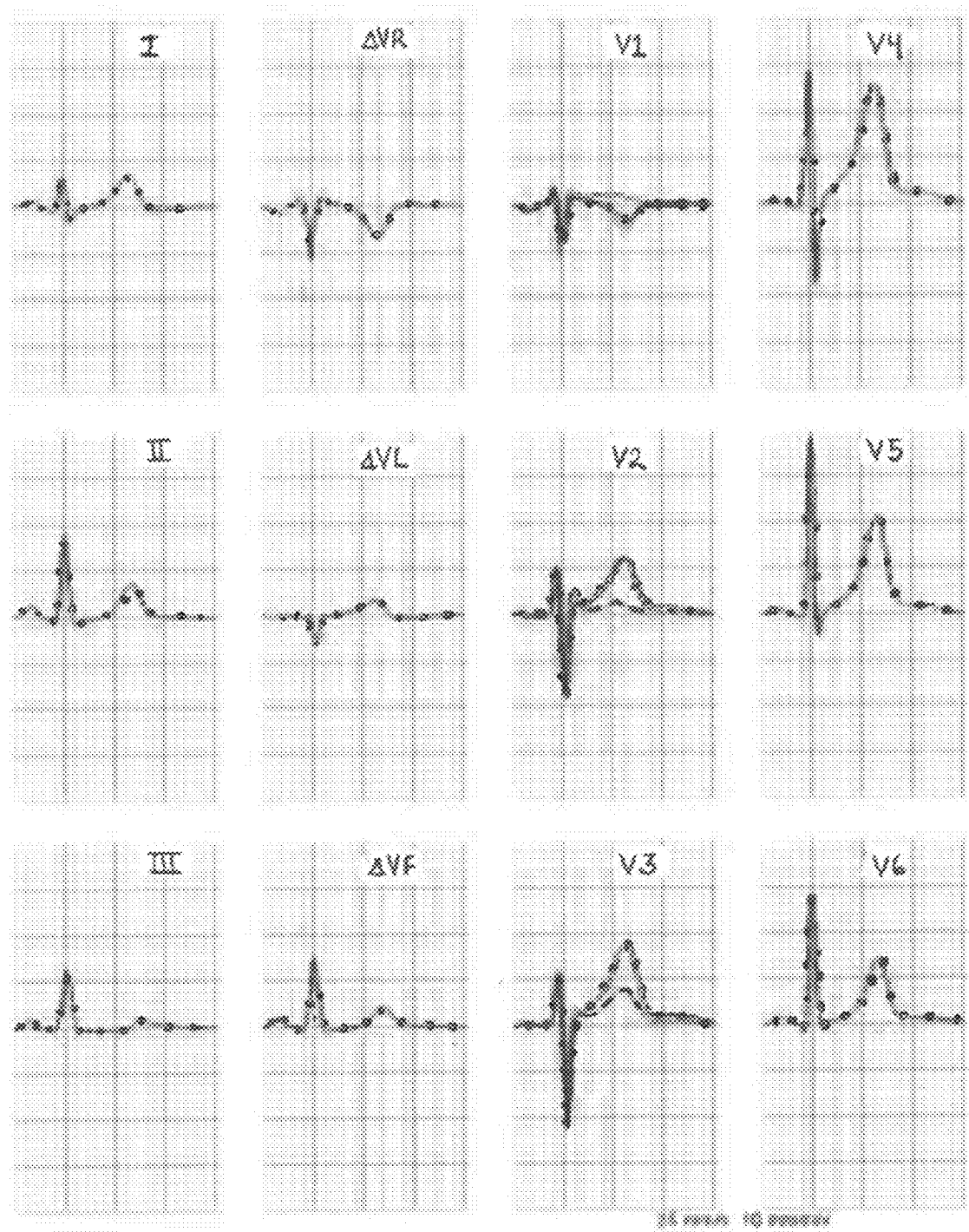
FIG. 12. Misplaced Lead Reconstruction: standard 12 lead ECG of case 5 (dotted line), misplaced electrode positions (dashed line), and reconstructed ECG at the standard positions (solid line). Note; V2 and V3 were completely reconstructed whereas V1 was not.

As an experiment, the geometrical information of the torso was used to correct the standard 12 lead ECG from the recorded misplaced ECG signals. In FIG. 11 is demonstrated the leads that need to be corrected are V1-4. In FIG. 12 is shown that the correction method proposed by Oostendorp et al. [17] corrected V2-3, but not V1. As shown in Table 2 the electrode configuration with V1,2 too high, V3 standard, and V4-6 too low produced a reduced match for four out of the five subjects. The new technique presented herein has created a new tool to improve the diagnostic accuracy of the standard 12 lead ECG.

New 3D camera computer software can automatically and rapidly detect misplacement of 12-lead ECGs recording in the EP lab and other locations and thereby increase the accuracy of the 12 lead ECG. The computer program is capable of correcting position information of most of these misplaced leads. This correction improves the results obtained from a diagnostic computerized ECG program.

Although the embodiments of the invention described with reference to the drawings comprise computer apparatus and processes performed in computer apparatus, the invention also extends to computer programs, particularly computer programs on or in a carrier, adapted for putting the invention into practice. The program may be in the form of source or object code or in any other form suitable for use in the implementation of the processes according to the invention. The carrier may be any entity or device capable of carrying the program.

For example, the carrier may comprise a storage medium, such as a ROM, for example a CD ROM or a semiconductor ROM, or a magnetic recording medium, for example a floppy disc or hard disk. Further, the carrier may be a transmissible carrier such as an electrical or optical signal which may be conveyed via electrical or optical cable or by radio or other means, e.g. via the internet or cloud.

When a program is embodied in a signal which may be conveyed directly by a cable or other device or means, the carrier may be constituted by such cable or other device or means. Alternatively, the carrier may be an integrated circuit in which the program is embedded, the integrated circuit being adapted for performing, or for use in the performance of, the relevant processes.

However, other modifications, variations, and alternatives are also possible. The specifications, drawings and examples are, accordingly, to be regarded in an illustrative sense rather than in a restrictive sense.

For the purpose of clarity and a concise description features are described herein as part of the same or separate embodiments, however, it will be appreciated that the scope of the invention may include embodiments having combinations of all or some of the features described.

In the claims, any reference signs placed between parentheses shall not be construed as limiting the claim. The word 'comprising' does not exclude the presence of other features or steps than those listed in a claim. Furthermore, the words 'a' and 'an' shall not be construed as limited to 'only one', but instead are used to mean 'at least one', and do not exclude a plurality. The mere fact that certain measures are recited in mutually different claims does not indicate that a combination of these measures cannot be used to an advantage.

REFERENCES

The following references are referred to above, and incorporated herein by reference.

[1] van Oosterom A, editor The Equivalent Surface Source Model in its Application to the T Wave. Electrocardiology'01; 2002: Univ Press São Paolo.

[2] van Oosterom A. The Equivalent Double Layer; Source Models for Repolarization. In: Macfarlane P W, van Oosterom A, Pahlm O, Kligfield P, Janse M C, Camm J, editors. Basic Electrocardiology. London: Springer; 2012. p. 227-46.

[3] Geselowitz D B. On the Theory of the Electrocardiogram. Proc IEEE. 1989; 77/6:857-76.

[4] Geselowitz D B. Description of cardiac sources in anisotropic cardiac muscle. Application of bidomain model. Journal of Electrocardiology. 1992; 25 Sup.: 65-7.

[5] Wilson F N, Macleod A G, Barker P S. The Distribution of Action Currents produced by the Heart Muscle and Other Excitable Tissues immersed in Conducting Media. J Gen Physiol. 1933; 16:423-56.

[6] Huiskamp G J H, van Oosterom A. The depolarization sequence of the human heart surface computed from measured body surface potentials. IEEE Transactions on Biomedical Engineering. 1988 December; 35(12):1047-58. PubMed PMID: 3220498.

[7] van Oosterom A. Genesis of the T wave as based on an equivalent surface source model. Journal of Electrocardiography. 2001; 34(Supplement 2001): 217-27.

[8] Meijs, Weier O W, Peters M J, van Oosterom A. On the Numerical Accuracy of the Boundary Element Method. IEEE Trans Biomed Eng. 1989; BME-36:1038-49.

[9] Swihart J J. Numerical Methods for solving the forward problem in electrocardiography. Nelson C V, Geselowitz D B, editors. Oxford: Clarendon Press; 1976.

[10] van Dam P M, Oostendorp T F, Linnenbank A C, van Oosterom A. Non-invasive imaging of cardiac activation and recovery. Annals Biomedical Engeneering. 2009; 37(9):1739-56.

[11] Huiskamp G J M, van Oosterom A. Heart position and orientation in forward and inverse electrocardiography. Med Biol Eng & Comput. 1992; 30:613-20.

[12] van Oosterom A, Huiskamp G J M. The Influence of Heart Position and Orientation on Body Surface Potentials. Proc XVII-th Int Conf Electrocardiol. 1990; 17:222-.

[13] van Dam P M, van Der Graaf A W M, Gotte M J W, editors. A new 3D patient specific morphing tool enabling clinical application of non-invasive cardiac activation imaging. ESC; 2012; Muenchen.

[14] van Dam P M, Oostendorp T F, van Oosterom A. Application of the fastest route algorithm in the interactive simulation of the effect of local ischemia on the ECG. Med Biol Eng Comput. 2009 January; 47(1):11-20. PubMed PMID: 18766396. Epub 2008 Sep. 4. eng.

[15] van Dam P M, Tung R, Shivkumar K, Laks M, Quantitative localization of premature ventricular contractions using myocardial activation ECGI from the standard 12-lead electrocardiogram, Journal of Electrocardiography, 2013, in press.

[16] Han J, Shao L, Xu D, Shotton, J Enhanced Computer Vision, Microsoft Kinect Sensor: A Review, IEEE Transactions on Systems, Man and Cybernetics, Part B, in press, 2013

[17] Oostendorp T F, van Oosterom A, Huiskamp G. Interpolation on a triangulated 3D surface. J Comput Phys. 1989; 80(2):331-43.

[18] Mahmoud K D, Gu Y L, Nijsten M W, de Vos R, Nieuwland W, Zijlstra F, et al. Interhospital transfer due to failed prehospital diagnosis for primary percutaneous coronary intervention: an observational study on incidence, predictors, and clinical impact. European Heart Journal: Acute Cardiovascular Care. 2013 Jun. 1, 2013; 2(2):166-75.

What is claimed is:

1. A computer implemented method for processing measurement data from 12-lead electrocardiogram, ECG, electrodes on an outer surface of a subject including the computer:
    obtaining a subject-specific three-dimensional, 3D, anatomical model of a heart and torso of the subject;
    obtaining, using a 3D camera, a three-dimensional photograph of an outer surface of the torso of the subject including position information of the electrodes on the outer surface of the torso of the subject;
    aligning the three dimensional photograph with the subject-specific three-dimensional model;
    determining a position of each electrode of the 12-lead ECG electrodes in the subject-specific three-dimensional model from the three dimensional photograph;
    automatically, using the 3D camera, determining an identification of each electrode;
    comparing detected electrode positions of the electrodes in the three-dimensional model with predetermined 12-lead ECG electrode positions;
    automatically determining a misplaced electrode relative to the predetermined 12-lead ECG electrode positions based on the comparison; and
    recording an ECG of the misplaced electrode and, responsive to the determining of electrode misplacement and using a torso geometry from the three-dimensional model, reconstructing from the ECG recorded of the misplaced electrode, a reconstructed ECG for an associated non-misplaced, predetermined 12-lead electrode position.

2. The method of claim 1, wherein the three-dimensional model of the torso of the subject is derived from a medical imaging system.

3. The method of claim 1, wherein the aligning includes minimizing distances between the three-dimensional photograph and the three-dimensional model.

4. The method of claim 1, further including determining the identification of each electrode from the three-dimensional photograph.

5. The method of claim 4, wherein the identification is one of a color, a shape, number, or a code.

6. The method of claim 1, further including determining whether electrodes are positioned in swapped positions.

7. The method of claim 6, further including swapping back signals of swapped electrodes.

8. The method of claim 1, including indicating whether the electrodes are positioned in a desired position.

9. The method of claim 8, further including indicating a direction and/or distance for repositioning an electrode to the desired position.

10. The method of claim 1, further including removing image data relating to a face of the subject from the three-dimensional photograph.

11. A system for processing measurement data from 12-lead electrocardiogram, ECG, electrodes on an outer surface of a subject, the system including:
    a model input device configured to obtain a subject-specific three-dimensional, 3D, anatomical model of a torso of the subject;
    a 3D photographic imaging device configured to obtain a three-dimensional photograph of an outer surface of the torso of the subject and arranged for determining an identification of each electrode;
    a processor configured to:
        align the three-dimensional photograph with the subject-specific three-dimensional model;

determine a position of each electrode of the 12-lead ECG electrodes in the subject specific three-dimensional model from the three-dimensional photograph;

compare detected electrode positions of the electrodes in the three-dimensional model with predetermined 12-lead electrode positions in the three-dimensional model;

automatically determine a misplaced electrode relative to the predetermined 12-lead ECG electrode positions based on the comparison; and record an ECG of the misplaced electrode and, responsive to the determining of electrode misplacement and using a torso geometry from the three-dimensional model, reconstruct from the ECG recorded of the misplaced electrode, a reconstructed ECG for an associated non-misplaced, predetermined 12-lead electrode position.

12. The system of claim 11 further including display means for displaying electrode positions in relating to the three-dimensional photograph and/or three-dimensional model.

13. The method of claim 4, further including determining the identification of each electrode by determining the electrode positioned closest to a predefined electrode location, and defining this electrode as coupled to the predefined electrode location.

\* \* \* \* \*